Nov. 11, 1952 R. L. BYRUM Plant Pat. 1,146
ROSE PLANT
Filed Nov. 9, 1951
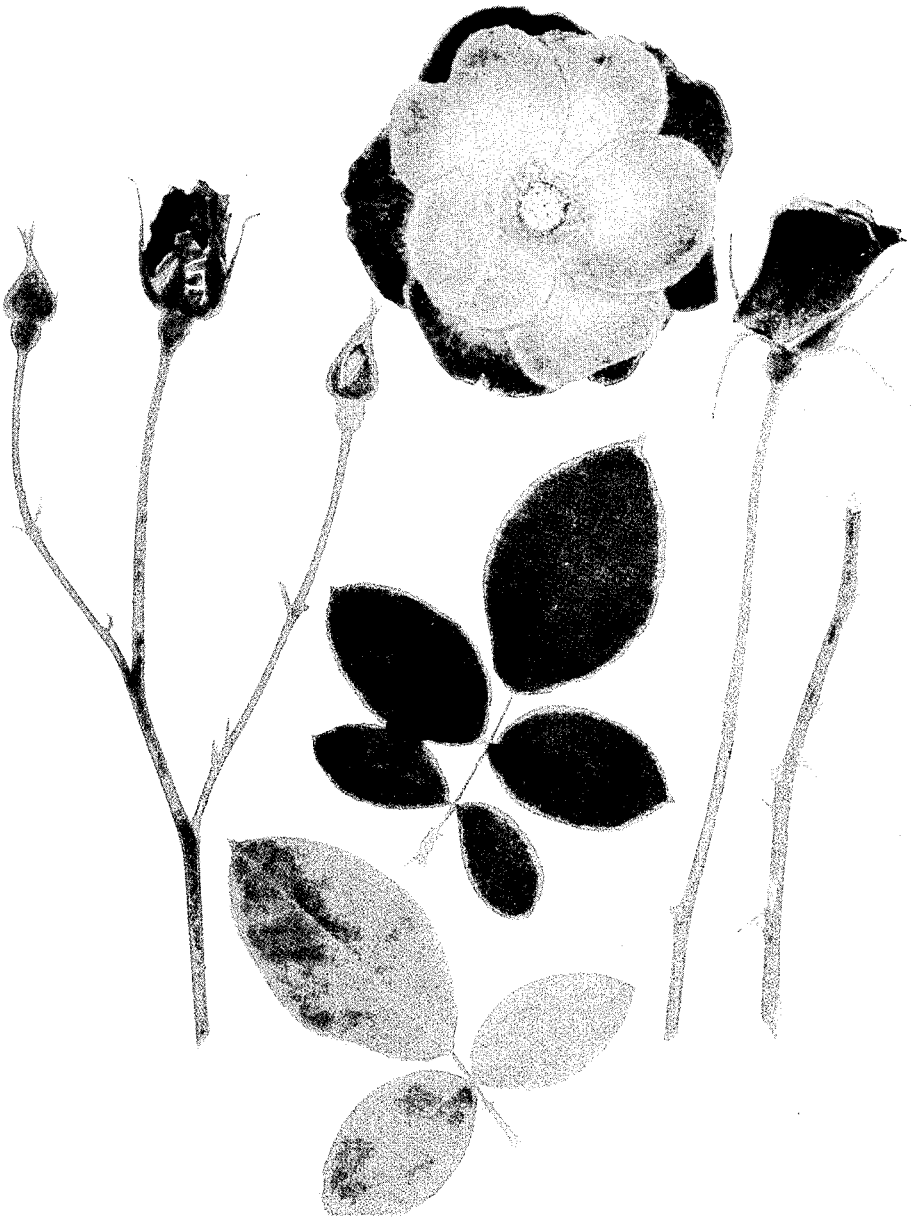
Inventor.
R. L. Byrum
By: Robert Cobb
Attorneys.

Patented Nov. 11, 1952

Plant Pat. 1,146

UNITED STATES PATENT OFFICE 1,146

ROSE PLANT

Roy L. Byrum, Richmond, Ind., assignor to Joseph H. Hill Company, Richmond, Ind., a corporation of Indiana Application November 9, 1951, Serial No. 255,604

1 Claim. (Cl. 47—61)

The present invention relates to a new and distinct variety of rose plant of the hybrid polyantha class, originated by me by crossing the hybrid polyantha variety "Baby Chateau" (unpatented) × the hybrid tea variety "Red Delicious" (Plant Patent No. 620).

As the result of this cross, I have produced an improved variety which, though it is primarily adapted for use as an outdoor rose and excels in this class, is also useful for forcing under glass.

The primary objective in making the aforementioned cross, was to produce a new variety of rose of the polyantha type, with flowers of a color comparable to the parent variety "Red Delicious," but having a stronger neck than the typical weak neck characteristics of this parent. This objective was fully achieved, as evidenced by the fact that the color of the flowers of my new variety is more nearly like "Red Delicious," but is a somewhat brighter red than the color of the flowers of either parent.

The parent variety "Red Delicious" is primarily a greenhouse forcing rose, and normally bears flowers singly to a stem, instead of in clusters. While the brilliant red color of this parent variety was very outstanding, it has not been too successful commercially by reason of the weakness of the neck, which has been eliminated in my new variety. In addition to the foregoing improved features of this new variety, it is a more vigorous grower than the variety "Baby Chateau," with the result that the plants of the new variety grow taller, and the flowers keep better than those of "Baby Chateau."

Briefly stated, the principal characteristics of this new variety which distinguish it from its parents, as well as from all other varieties heretofore known in commerce, are the abundance and the extra bright color of its flowers, combined with the exceptional good-keeping qualities thereof.

Asexual reproduction of my new variety by cuttings, grafting and budding at Richmond, Indiana, shows that the foregoing characteristics come true to form and are established and transmitted through succeeding propagations.

The accompanying drawing shows specimen flowers of the new variety in various stages of development from tight bud to fully open, as well as upper and lower surfaces of typical foliage specimens, and also a short section of a specimen stem with a typical thorn arrangement.

The following is a detailed description of my new variety, with color terminology in accordance with Wilson's Horticultural Colour Chart, except where specifically noted as being in accordance with Koster's Color Guide or where general color terms of ordinary dictionary significance are obvious:

Type: Hardy; bush; outdoor seedling; for garden decoration and for cut flowers; also useful for forcing in the greenhouse.

Class: Hybrid polyantha.

Parentage:

*Seed parent.*—"Baby Chateau."

*Pollen parent.*—"Red Delicious."

Propagation: Holds its distinguishing characteristics through succeeding propagations by cuttings, grafting and by budding.

*Flower*

Locality where grown and observed: Richmond, Indiana.

Flowers borne: Several to a stem, in irregular clusters; on strong, medium length stems.

Quantity of bloom: Abundant both outdoors and in the greenhouse.

Continuity: Continuous.

Fragrance: Slight tea.

Bud:

*Peduncle.*—Short; medium heavy; erect; stiff; smooth bark. Color—Purple Madder, Plate 1028/1. Prickles—numerous; color—Oxblood Red, Plate 00823/2.

*Before calyx breaks.*—Size—medium. Form—short; pointed; ovoid, with a conspicuous neck; with foliaceous appendages on the surface of the bud; with slender, bristle-like foliaceous parts extending beyond the tip of the bud equal to one-fourth or more of its length.

*As first petal opens.*—Size—small. Form—short; pointed. Color: outside—Oxblood Red, Plate 00823; inside—Base Cardinal Red, Plate 822, shading into Oxblood Red, Plate 00823.

*Opening.*—Opens up well.

Bloom:

*Size when fully open.*—Medium; two to three inches.

*Petalage.*—Semi-double; 10 to 12 petals regularly arranged.

*Form.*—Flat; open.

Petals: Thick; leathery; with inside velvety and outside satiny.

*Shape.*—Outside—obovate, with apex mucronate. Intermediate—petals vary; some are notched, some are wavy, obovate, with apex mucronate.

This description of a newly opened flower was made from a rose grown outdoors in the month of September, at Richmond, Indiana:

*Color.*—Outside petal: outside surface—Rose Red, Plate 724/1; some with white streaks in center; inside surface—Crimson, Plate 22, with velvety appearance. Intermediate petal: outside surface—Rose Red, Plate 724; inside surface—Cherry, Plate 722; some lightly penciled with velvety streaks.

This description was made from a rose that was open for three days outdoors in the month of September, at Richmond, Indiana:

*Color.*—Outside petal: outside surface—Rose Red, Plate 724/2 to 724/3; inside surface—Cherry, Plate 722/3, blotched with Rose Red, Plate 724/2; lightly penciled with velvety streaks. Inside petal: outside surface—Rose Red, Plate 724/2 to 724/3; inside surface—Cherry, Plate 722/3, blotched with Rose Red, Plate 724/2; lightly penciled with velvety streaks.

*General color effect.*—Newly opened flower—Cherry, Plate 722. Three days open—Rose Red, Plate 724/1 through 724/3.

*Behavior.*—Persists.

*Flower longevity.*—Flowers on the bush outdoors—5 days or more in June and August. Cut flowers grown outdoors kept at living-room temperature—7 days in July.

*Reproductive organs*

Stamens: Many; arranged irregularly about pistils.

Filaments: Long; most with anthers. Color—Cherry, Plate 722/3.

Anthers: Small; all open at once. Color—Yellow Ochre, Plate 07.

Pollen: Abundant. Color—Cadmium Orange, Plate 8/2.

Pistils: Many.

Styles: Uneven; medium length; medium heavy; bunched.

Stigma: White.

Ovaries: Some protruding from Calyx.

Sepals: Permanent; moderately long; spear-shaped; curled. Color: inside—Cypress Green, Plate 59/1, overlaid with white fuzz; outside—Scheeles Green, Plate 860/2, blotched with bronze.

*Plant*

Foliage:

*Leaves.*—Compound of 3 and 5; abundant; moderately large; heavy; leathery; wrinkled.

*Leaflets.*—Oblong, with apex mucronate; base round; margin simply serrate.

*Color.*—Mature: upper surface—near Parsley Green, Plate 00962; under surface—near Spinach Green, Plate 0960/3. Young: upper surface—near Oxblood Red, Plate 00823/3; under surface—near Oxblood Red, Plate 00823/3.

*Rachis.*—Heavy. Upper side — grooved. Under side—almost smooth; 3 to 5 prickles.

*Stipules.*—Moderately long; medium width; with short points turning out at an angle of less than 45°.

*Disease.*—Resistant to mildew and blackspot, as determined by comparison with other varieties of the same class grown under comparable conditions at Richmond, Indiana.

Growth:

*Habit.*—Bush; upright; much branched.

*Growth.*—Vigorous.

*Canes.*—Heavy.

*Main stems.*—Color—near Spinach Green, Plate 0960/2. Thorns — many; medium length; hooked downward; with long, narrow base; color—Van Dyke Brown, Plate 96, Koster Color Guide. Prickles—several; color—Van Dyke Brown, Plate 96, Koster Color Guide. Hairs—none.

*Branches.*—Color — near Spinach Green, Plate 096/3. Thorns — several; long; hooked downward; with long, narrow base; color—near Oxblood Red, Plate 00823/1. Prickles—several; color—Oxblood Red, Plate 00823/2. Hairs—few; color—Oxblood Red, Plate 00823/2.

*New shoots.*—Color—near Oxblood Red, Plate 00823/2. Thorns—several; long; hooked downward; with long, narrow base; color—near Oxblood Red, Plate 00823/2. Prickles—several; color—Oxblood Red, Plate 00823/3. Hairs—few; color—Oxblood Red, Plate 00823/3.

I claim:

A new and distinct variety of rose plant of the hybrid polyantha class, substantially as herein shown and described, particularly characterized as to novelty by the abundance of its blooms, by the extra bright color thereof, and by the extra good-keeping qualities of its blooms.

ROY L. BYRUM.

No references cited.